United States Patent [19]

Fabry et al.

[11] Patent Number: 4,981,617

[45] Date of Patent: Jan. 1, 1991

[54] PROCESS FOR THE PREPARATION OF REACTION PRODUCTS OF EPOXIDIZED RICINOLEIC ACID GLYCERIDES WITH SULFUR TRIOXIDE

[75] Inventors: Bernd Fabry, Korschenbroich; Robert Piorr, Ratingen-Hoesel; Frank Clasen, Hilden; Horst Ritterbex; Hans Bornmann, both of Duesseldorf, all of Fed. Rep. of Germany

[73] Assignee: Henkel Kommanditgesellschaft auf Aktien, Duesseldorf-Hilthausen, Fed. Rep. of Germany

[21] Appl. No.: 240,772

[22] Filed: Sep. 2, 1988

[30] Foreign Application Priority Data

Sep. 3, 1987 [DE] Fed. Rep. of Germany ....... 3729484

[51] Int. Cl.$^5$ .................. C07C 309/00; C07C 311/00
[52] U.S. Cl. .................................... 260/400; 260/401
[58] Field of Search .............................. 260/400, 407

[56] References Cited

U.S. PATENT DOCUMENTS

| | | | |
|---|---|---|---|
| 3,158,632 | 11/1964 | Blaser | 260/400 |
| 3,159,657 | 12/1964 | Wulff et al. | 260/400 |
| 3,300,525 | 1/1967 | Plapper et al. | 260/400 |
| 3,891,689 | 6/1975 | Pryce | 260/400 |
| 3,969,375 | 7/1976 | Okamura et al. | 260/400 |

FOREIGN PATENT DOCUMENTS

| | | | |
|---|---|---|---|
| 738447 | 7/1966 | Canada | 260/400 |
| 0178557 | 10/1985 | European Pat. Off. | |
| 0222237 | 10/1986 | European Pat. Off. | |
| 0241839 | 4/1987 | European Pat. Off. | |
| 0247509 | 12/1987 | European Pat. Off. | 260/400 |
| 1443989 | 9/1962 | Fed. Rep. of Germany | |
| 2040503 | 2/1972 | Fed. Rep. of Germany | |
| 3617657 | 5/1986 | Fed. Rep. of Germany | |
| 3612481 | 10/1987 | Fed. Rep. of Germany | 260/400 |
| 979334 | 12/1982 | U.S.S.R. | 260/401 |
| 1050534 | 12/1966 | United Kingdom | 260/400 |

OTHER PUBLICATIONS

Journal of Organic Chemistry, 25, 864, (1960).
Encyclopedia of Chem. Techn., 2. Aufl., Bd. 19, pp. 301–306.
Chem. Technologie 4. Aufl. Bd. 4, pp. 464–468, (no translation).

*Primary Examiner*—John Kight, III
*Assistant Examiner*—Dennis R. Daley
*Attorney, Agent, or Firm*—Ernest G. Szoke; Wayne C. Jaeschke; Real J. Grandmaison

[57] ABSTRACT

The sulfonation of epoxidized ricinoleic acid glycerides with a dry stream of gaseous sulfur trioxide diluted with a carrier gas, followed by a reaction of the sulfonated reaction product with nucleophiles, leads to salt-free and anhydrous products showing surface-active properties.

24 Claims, No Drawings

PROCESS FOR THE PREPARATION OF REACTION PRODUCTS OF EPOXIDIZED RICINOLEIC ACID GLYCERIDES WITH SULFUR TRIOXIDE

BACKGROUND OF THE INVENTION

1. Field of the Invention

This invention relates to a process for the production of reaction products of epoxidized ricinoleic acid glycerides with sulfur trioxide. The products prepared in accordance with the invention show surface-active properties and may be used as emulsifiers and as constituents of detergents.

2. Statement of Related Art

Functional groups may be introduced into a molecule of unsaturated fatty acid esters using known methods such as by conversion of the olefinic double bonds of these compounds into an oxirane ring by epoxidation, followed by opening of the oxirane ring with nucleophiles to form 2-hydroxyalkyl derivatives.

It is also known that epoxides may be converted into 1,2-glycol sulfates by reaction with sulfur trioxide. In the case of ethylene oxide, however, this reaction is so violent according to J. Org. Chem. 25, 864 (1960) that the direct reaction with sulfur trioxide is accompanied by decomposition. The reference indicates that only the reaction with a sulfur trioxide/dioxide adduct leads to the desired glycol sulfate. German Patent Document DE-AS 20 40 503 discloses first reacting the epoxide with sulfur dioxide to form the glycol sulfite followed by further reaction with sulfur trioxide to form the glycol sulfate.

An important species of the above-mentioned reaction products of epoxy fatty acid esters with sulfur trioxide is that obtained using epoxidized castor oil as the epoxy reactant. This compound is prepared by sulfatization of epoxidized castor oil with oleum. However, this process generates by-products having a high salt content which is undesirable from the environmental wastewater standpoint. In addition, the products obtained by this process contain a considerable concentration of sulfate which can be very corrosive. Similar disadvantages attend sulfonation processes which use sulfuric acid or chlorosulfonic acid. Such processes, and the above mentioned oleum sulfonation process, are described in Kirk-Othmer, Encyclopedia of Chemical Technology, 2nd Edition, Vol. 19, pages 301 to 306, J. Wiley & Sons, New York, 1983 and in Winnacker-Kuechler, Chemische Technologie, 4th Edition, Vol. 4, pages 464 to 468, Carl Hanser Verlag, Munchen, 1984.

DESCRIPTION OF THE INVENTION

Other than in the operating examples, or where otherwise indicated, all numbers expressing quantities of ingredients or reaction conditions used herein are to be understood as modified in all instances by the term "about".

The present invention is directed to a process for the production of reaction products of epoxidized ricinoleic acid glycerides with sulfur trioxide by which the salt pollution of wastewaters and end products is essentially avoided. It has been found that the direct reaction of epoxy fatty acids with sulfur trioxide can be made to take place smoothly with no decomposition phenomena under conditions as hereinafter described. The sulfur trioxide initially reacts very rapidly with the epoxy groups present to form 1,2-glycol sulfate groups and reacts at a lower reaction velocity with the hydroxyl groups present in the ricinoleic residues to form ricinoleic sulfate groups. These latter groups are accessible to subsequent reactions with nucleophiles to form products exhibiting surface-active properties.

According to the process of the present invention, epoxidized ricinoleic acid glycerides are reacted with a dry stream of gaseous sulfur trioxide diluted with a carrier gas and the sulfonated reaction product is reacted with nucleophiles. The above described undesired salt accumulation does not occur in the process of this invention since there is no need to neutralize excess sulfuric acid.

The epoxidized ricinoleic acid glycerides which may be used in this invention are preferably those obtained by epoxidation of castor oil in which the fatty acid component contains certain proportions of saturated and/or unsaturated fatty acids. It is preferred to use a partially epoxidized castor oil in which 10 to 30%, and more preferably 10 to 15%, of the olefinic double bonds originally present are epoxidized. Partial glycerides of the epoxidized ricinoleic acid may also be used.

The sulfonation process according to this invention is carried out by reacting the epoxidized ricinoleic acid glycerides with gaseous sulfur trioxide diluted in a carrier gas. The preferred carrier gases are air or nitrogen. preferably, the gas stream has a sulfur trioxide content of 2 to 10% by volume, more preferably of 5 to 18% by volume. The reaction temperature in the sulfonation reaction is preferably from 30° to 80° C. and more preferably from 40° to 50° C. At temperatures below 30° C., the epoxidized castor oil glycerides are very difficult to sulfatize. By contrast, at temperatures above 80° C., there occur unwanted secondary reactions including ester cleavages, coking and distinct deterioration in the color of the product.

It is preferred to react 0.25 to 1 mol of sulfur trioxide per mol of ricinoleic acid residue. The reaction may be conducted in the presence or absence of solvents. Where the reaction is carried out in the absence of solvents, the sulfur trioxide is preferably used in a molar ratio of 0.25 to 0.6. Where more than 0.6 mol sulfur trioxide is used, the viscosity of the reaction product increases to the point where the presence of one or more inert solvents is required to guarantee an adequate uptake of sulfur trioxide. The solvents preferably used are low-boiling, readily separable solvents, including chlorinated hydrocarbons.

The sulfonation reaction is preferably carried out in a sulfonation flask or tank equipped with a powerful mechanical stirrer and an intensive jacket cooling or internal cooling system to guarantee thorough mixing of gas and liquid phases, optimal dissipation of heat and, hence, high conversion levels. The reaction time is preferably between 1 and 1.5 hours.

The crude sulfonation product obtained as described above is cooled and subsequently reacted with one or more nucleophiles (nucleophilic agents) selected from the group consisting of hydroxyl, alcoholate, phenolate and carboxylate ions, ammonia, and primary, secondary and tertiary amines. The sulfonated reaction products may be subsequently neutralized preferably using aqueous bases selected from the group consisting of aqueous solutions of oxides, hydroxides and carbonates of the alkali and alkaline earth metals, and ammonia. Neutralization is preferably carried out using the aqueous bases in excess, preferably up to 30% in excess, and more preferably up to 20% in excess, based on the uptake of sulfur trioxide. Preferred neutralization conditions are heating the mixture of base and sulfonated reaction products at 100° C. for 1 to 4 hours. It is also preferred to add a bleach during the neutralization step, such as 1 to 1.5% by weight of a 35% by weight solution of hydrogen peroxide.

To separate the salts formed during the reaction with nucleophiles or during neutralization, it is normally not sufficient to wash out the product with water by conventional methods because this leads to the formation of a stable emulsion which cannot be completely broken up using standard de-emulsifiers. Products obtained by this method also show a high salt concentration and may contain up to 50% water. Accordingly, the sulfonated reaction product reacted with nucleophiles or with aqueous bases is freed from insoluble reaction products by addition of one or more water-miscible organic solvents and isolated by the removal of the organic solvent. Preferred water-miscible solvents include alcohols selected from the group consisting of $C_1$-$C_5$ monoalcohols, ethylene glycol, propylene glycol, glycerol and ketones. It is particularly preferred to use monohydric alcohols containing 3 to 4 carbon atoms, such as 1-propanol, 2-propanol, butanol and like solvents. These solvents may be added in a quantity of 20 to 60% by weight, preferably in a quantity of 30 to 50% by weight and more preferably in a quantity of 35 to 40% by weight. After addition of the water-miscible organic solvents, the resulting mixture is heated. The neutralization salts subsequently completely precipitate as a consequence of altered solubilities and may be separated by any suitable technique such as by filtration.

The water-miscible organic solvents may then be distilled off in vacuo at 100° C. The product thus obtained is a clear, light yellow 100% oil.

The invention is illustrated by the following Examples and Comparative Examples.

EXAMPLE 1

(a) Reaction of partially epoxidized castor oil with sulfur trioxide 600 g (0.65 mol) of epoxidized castor oil (saponification value SC=182.4 iodine value IV=61.0, epoxide value EpV=0.53%, molecular weight from SC=922.9) were introduced into a 1 liter sulfonation flask equipped with a gas inlet pipe, metal propeller stirrer and jacket cooling system and sulfonated at 50° C. by introducing 78 g (0.975 mol) of $SO_3$.

The $SO_3$ was introduced by heating a corresponding quantity of oleum to release $SO_3$, diluted with nitrogen gas to a concentration of 5% by volume and introduced into the inlet over a period of 60 minutes, the temperature of the reaction mixture being kept at values below 60° C. by cooling the flask.

After the sulfonation, the acidic reaction mixture was cooled to 10° C. and reacted with a concentrated solution of 22 g (1.3 mol) ammonia in 150 ml water.

(b) Neutralization and isolation of the sulfonated epoxidized castor oil

The reaction mixture obtained in stage (a) was hydrolyzed on a water bath for 2 hours at 95°-100° C. The mixture was then dissolved while stirring in 235 g (3.9 mol) isopropyl alcohol at 70° C., whereupon the neutralization salts precipitated out of solution.

The precipitated neutralization salts were separated in a vacuum filter and the filtrate transferred to a distillation apparatus where the fractions of isopropyl alcohol and aqueous ammonia were removed at 15 torr/90° C.

The product obtained had the following characteristic composition:

Anionic surfactant (two-phase titration by Einheitsmethode (Standard Method)
DGF-H-III-10: 0.906 mval/g
Unsulfonated fractions (DGF-G-III-6b): 4.5% by wt.
Sulfate (expressed as sodium sulfate): <0.05% by wt.
Chloride: <0.05% by wt.
Water (FISCHER's method): 0.9% by wt.

COMPARATIVE EXAMPLE 2

The reaction mixture obtained in Example 1, stage a, was hydrolyzed on a water bath for 2 hours at 95°-100° C. 670 g of water, 300 g of saturated sodium chloride solution and 10 ml of the demulsifier DEHYDRAN TM 241 were added to the solution which was then heated on a steam bath for about 1.5 hours at 95°-100° C.

After phase separation, the heavier aqueous phase was separated and discarded. The upper organic phase still containing some of the water in the form of an emulsion was transferred to a distillation apparatus where the sulfonation product was dehydrated at 15 torr/90° C.

The product obtained had the following characteristic composition:

(a) Before distillation:
Anionic surfactant (two-phase titration by Standard Method DGF-H-III-10): 0.613 mval/g
Unsulfonated fractions (DGF-G-III-6b): 3.6% by wt.
Sulfate (expressed as sodium sulfate): 0.6% by wt.
Chloride: 0.2% by wt.
Water (FISCHER's method): 33% by wt.

(b) After distillation:
Anionic surfactant (two-phase titration by Standard Method DGF-H-III-10): 0.897 mval/g
Unsulfonated fractions (DGF-G-III-6b): 5.5% by wt.
Sulfate (expressed as sodium sulfate): 0.7% by wt.
Chloride: 0.2% by wt.
Water (FISCHER's method): 2% by wt.

Comparison of the above characteristic composition with that of the product of Example 1 shows that the product obtained in accordance with the invention has a higher content of anionic surfactant, a lower salt content and a lower water content than the product obtained in accordance with this Example.

COMPARATIVE EXAMPLE 3

The reaction mixture obtained in accordance with Example 1, stage a, was hydrolyzed on a water bath for 2 hours at 95°-100° C. The solution was then transferred to a distillation apparatus where 143 ml water and excess ammonia not reacted during neutralization were distilled off at 15 torr/90° C., so that the product had a residual water content of around 5%.

The neutralization salts which precipitated during the concentration step were then separated off at 95° C. in a super-heated-stream vacuum filter using a filter aid. The product obtained had the following characteristic composition:

Anionic surfactant (two-phase titration by Standard Method DGF-H-III-10) : 0.868 mval/g
Unsulfonated fractions (DGF-G-III-6b) : 5.2% by wt.
Sulfate (expressed as sodium sulfate) 1.1% by wt.
Chloride :<0.05% by wt.
Water (FISCHER's method) : 5% by wt.

Comparison of the characteristic composition with Example 1 shows that the product obtained in accordance with the invention has a higher anionic surfactant content and lower salt and water contents than the product obtained in accordance with this Example.

COMPARATIVE EXAMPLE 4

Reaction of epoxidized castor oil with sulfuric acid 600 g (0.65 mol) of epoxidized castor oil (epoxide value 1.49%) were introduced into a 1 liter sulfonation flask equipped with a metal propeller stirrer and jacket cooling system and 96 g (0.975 mol) of 98% sulfuric acid was then added in portions with intensive stirring so that the temperature of the solution did not exceed 60° C. After addition of the sulfatizing agent over a period of 4 hours, the mixture was stirred for another hour at 50° C. and then adjusted to a pH of 2.2 with aqueous ammonia solution, at which point phase separation occurred. The aqueous phase containing the salts formed during the partial neutralization and also the excess sulfuric acid was separated off and discarded. The residual organic phase was adjusted to a pH of 7-7.4 with concentrated ammonia. The product obtained had the following characteristic composition:
Anionic surfactant (two-phase titration by Standard method DGF-H-III-10): 0.557 mval/g
Unsulfonated fractions (DGF-G-III-6b): 21.9% by wt.
Sulfate (expressed as sodium sulfate): 1.2% by wt.
Chloride: 0.05% by wt.
Water (FISCHER's method): 20.2% by wt.

Comparison of this product with that of Example 1 shows in particular the low anionic surfactant content, the high content of unsulfonated fractions and also the high water content of the product obtained in accordance with this Comparative Example.

EXAMPLE 5

Reaction of epoxidized castor oil with sulfur trioxide in 1,2-dichloroethane 3 g (0.66 mol) of sulfur trioxide were introduced into 50 ml 1,2-dichloroethane and dissolved in the solvent at 0° C. 300 g (0.32 mol) of an epoxidized castor oil (epoxide value 0.53) were introduced into a 500 ml three-necked flask equipped with a metal propeller stirrer, dropping funnel and internal thermometer and dissolved in approximately 350 ml predried 1,2-dichloroethane. The prepared solution of the $SO_3$ in the organic solvent was added dropwise with intensive stirring over a period of time of about 60 minutes and at such a rate that the temperature of the solution did not rise above 20° C. The solvent was then distilled off very quickly at 30° C. in a high vacuum, the acidic ester was neutralized with 13.5 g (0.8 mol) $NH_3$ in 120 ml water and then isolated as in Example 1, stage b.

The product obtained had the following characteristic composition:
Anionic surfactant (two-phase titration by Standard Method DGF-H-III-10): 0.88 mval/g
Unsulfonated fractions (DGF-G-III-6b): 14.5% by wt.
Sulfate (expressed as sodium sulfate): 1.8% by wt.
Chloride: <0.05% by wt.
Water (FISCHER's method): 0.9% by wt.

EXAMPLE 6

Reaction of epoxidized ricinoleic acid monoglyceride with sulfur trioxide 335 g (1.00 mol) epoxidized castor oil monoglyceride (saponification value SC=167.5, epoxide value EpoV =1.49%, molecular weight from SV=334.9) were initially introduced into a 1 liter sulfonation flask equipped with a gas inlet pipe, metal propeller stirrer and jacket cooling system and sulfonated with 40 g (0.35 mol) of sulfur trioxide at 50° C. The $SO_3$ was obtained as described in Example 1, stage a, and was introduced into the inlet over a period of 35 minutes diluted with nitrogen gas to a concentration of 5% by volume, during which the temperature of the reaction mixture was kept below 60° C. by cooling. After sulfonation, the acidic reaction mixture was cooled to 10° C., reacted with a concentrated solution of 9 g (0.48 mol) $NH_3$ in 75 ml water and then isolated as described in Example 1, stage b. The product obtained had the following characteristic composition:
Anionic surfactant (two-phase titration by Standard Method DGF-H-III-10) : 2.65 mval/g
Unsulfonated fractions (DGF-H-III-6b) : 9.8% by wt.
Sulfate (expressed as sodium sulfate) : 0.4% by wt.
Chloride :<0.05% by wt.
Water (FISCHER's method) : 0.9% by wt.

It is to be understood that the above described embodiments of the invention are illustrative only and that modifications throughout may occur to those skilled in the art.

We claim:

1. A process for preparing sulfonated derivatives of epoxidized ricinoleic acid glycerides having surface-active properties comprising contacting an epoxidized castor oil glyceride with a dry, gaseous stream of sulfur trioxide diluted with a carrier gas under conditions of agitation and for a period of time and at a temperature sufficient to produce a sulfonated reaction product, reacting said sulfonated reaction product with a nucleophilic agent, dissolving the sulfonated reaction product reacted with said nucleophilic agent in a water-miscible organic solvent, heating the resulting mixture to precipitate salt impurities therefrom, separating the precipitated salt impurities from the mixture, and isolating said sulfonated reaction product reacted with said nucleophilic agent by removal of said organic solvent.

2. The process of claim 1, wherein said carrier gas is air or nitrogen.

3. The process of claim 2 wherein said carrier gas is nitrogen.

4. The process of claim 1, wherein said nucleophilic agent is selected from the group consisting of hydroxyl, alcoholate, phenolate and carboxylate ions, ammonia, and primary, secondary and tertiary amines.

5. The process of claim 1 wherein said carrier gas stream has a sulfur dioxide content of from about 2 to about 10% by volume.

6. The process of claim 5 wherein said carrier gas stream has a sulfur dioxide content of from about 5 to about 8% by volume.

7. The process of claim 1 wherein the epoxidized castor oil gylceride is reacted with the sulfur trioxide at a temperature of from about 30° to about 80° C.

8. The process of claim 7 wherein the epoxidized castor oil glyceride is reacted with the sulfur trioxide at a temperature of from about 40° to about 50° C.

9. The process of claim 1 wherein at least about 0.25 to about 1 mol sulfur trioxide is used per mol ricinoleic acid present in the castor oil residue.

10. The process of claim 1 wherein from about 0.25 to about 0.6 mol of sulfur trioxide is used per mol ricinoleic acid present in the castor oil residue.

11. The process of claim 1 wherein said epoxidized castor oil glyceride is dissolved in organic solvent during the reaction with said sulfur trioxide.

12. The process of claim 11 wherein from about 0.6 to about 1.0 mol of sulfur trioxide is used per mol ricinoleic acid present in the castor oil residue.

13. The process of claim 1 wherein the reaction with sulfur trioxide is carried out over a period of from about 1 to about 1.5 hours.

14. The process of claim 1 wherein the sulfonated reaction products are neutralized with an aqueous base selected from the group consisting of oxides, hydroxides and carbonates of alkali and alkaline earth metals, and ammonia.

15. The process of claim 14 wherein the aqueous base is present in an excess of up to about 30%.

16. The process of claim 15 wherein the aqueous base is present in an excess of up to about 20%.

17. The process of claim 14 wherein a bleach is present during said neutralization process.

18. The process of claim 1 wherein said watermiscible organic solvent is selected from the group consisting of $C_1$–$C_5$ monoalcohols, ethylene glycol, proplene glycol, glycerol, ketones and mixtures thereof.

19. The process of claim 18, wherein said organic solvent is one or more monohydric alcohols containing 3 to 4 carbon atoms.

20. The process of claim 1 wherein the water-miscible organic solvent is present at a level of about 20 to about 60% by weight of said reaction product.

21. The process of claim 20 wherein the water-miscible organic solvent is present at a level of about 30 to about 50% by weight of said reaction product.

22. The process of claim 1 wherein said castor oil glyceride is epoxidized to the extent of about 10 to about 30% of the olefinic double bonds originally present.

23. The process of claim 22 wherein said castor oil glyceride is epoxidized to the extent of about 10 to about 15% of the olefinic double bonds originally present.

24. The process of claim 1 wherein said epoxidized castor oil glyceride is a monoglyceride.

* * * * *

UNITED STATES PATENT AND TRADEMARK OFFICE
CERTIFICATE OF CORRECTION

PATENT NO. : 4,981,617

DATED : 1/1/91

INVENTOR(S) : Bernd Fabry et al.

It is certified that error appears in the above-identified patent and that said Letters Patent is hereby corrected as shown below:

In Claim 18, Column 8, line 5, "proplene" should read --propylene--.

Signed and Sealed this

Twenty-ninth Day of September, 1992

*Attest:*

DOUGLAS B. COMER

*Attesting Officer*     *Acting Commissioner of Patents and Trademarks*